(12) United States Patent  (10) Patent No.: US 6,966,909 B2
Marshall et al.  (45) Date of Patent: Nov. 22, 2005

(54) SURGICAL INSTRUMENT

(75) Inventors: Mark George Marshall, Winnersh (GB); Colin Charles Owen Goble, Egham (GB)

(73) Assignee: Gyrus Medical Limited, Cardiff (GB)

(*) Notice: Subject to any disclaimer, the term of this patent is extended or adjusted under 35 U.S.C. 154(b) by 321 days.

(21) Appl. No.: 10/382,831

(22) Filed: Mar. 7, 2003

(65) Prior Publication Data

US 2003/0176858 A1  Sep. 18, 2003

(30) Foreign Application Priority Data

Mar. 15, 2002 (GB) .................................. 0206208

(51) Int. Cl.⁷ ............................................... A61B 18/14
(52) U.S. Cl. .................... 606/41; 45/49; 45/51; 45/52; 29/825

(58) Field of Search ....................... 606/41–52; 29/825

(56) References Cited

U.S. PATENT DOCUMENTS

| 5,342,381 | A |   | 8/1994  | Tidemand |
| 5,810,811 | A | * | 9/1998  | Yates et al. .................... 606/50 |
| 5,816,471 | A | * | 10/1998 | Plyley et al. ............. 227/178.1 |
| 6,039,735 | A | * | 3/2000  | Greep .......................... 606/45 |

* cited by examiner

*Primary Examiner*—Lee S. Cohen
(74) *Attorney, Agent, or Firm*—Oliff & Berridge, PLC

(57) ABSTRACT

An electrosurgical instrument for use in cutting and/or coagulating tissue includes one or more electrode surfaces (15 and 16) at least partly coated with tungsten disulphide. The tungsten disulphide coating acts to reduce the incidence of tissue becoming adhered to the or each electrode surface (15, 16). Examples of electrosurgical instruments employing such coated electrodes include forceps, scissors or scalpel blade instruments.

8 Claims, 4 Drawing Sheets

SURGICAL INSTRUMENT

This invention relates to an electrosurgical instrument such as a forceps, scissors or scalpel blade, and to non-stick coatings therefor. Such instruments are commonly used for the coagulating or cutting of tissue in surgical intervention, most commonly in "keyhole" or minimally invasive surgery, but also in "open" surgery.

A problem arises in the use of such instruments when tissue adheres to the electrosurgical electrode. Cut or charred tissue can collect on the electrode or electrodes, interfering with the performance of the instrument. Various non-stick coatings have been developed to try to alleviate this problem, the most common materials for such coatings being Teflon® or ceramic materials such as titanium nitride.

The present invention seeks to provide an alternative to such prior art coatings.

The present invention provides an electrosurgical instrument including one or more electrode surfaces, at least one of the electrode surfaces being at least partially coated with tungsten disulphide. The tungsten disulphide coating has been found to have surprisingly good properties when it comes to preventing tissue from adhering thereto.

Tungsten disulphide is known as a low friction material. It is available from sources such as Brycoat Inc, Dicronite Dry Lube and WS2 Coatings Limited. However, up to now, it has been primarily used as a coating for gears and bearings, or as a mould release agent in the injection moulding of plastics materials. The potential for the use of tungsten disulphide as a non-stick coating in electrosurgical instruments has only now been identified by the present applicants.

The invention further resides in an electrosurgical instrument for use in cutting and/or coagulating tissue, the instrument comprising at least one electrode, the or each electrode comprising a substrate adapted to be connected to a source of radio frequency energy, and a tungsten disulphide coating disposed on the substrate.

Preferably, the tungsten disulphide coating is a spray deposited coating.

According to a preferred construction, the electrosurgical instrument is a bipolar electrosurgical instrument, and comprises first and second electrodes, the first electrode providing a path for the radio frequency energy to travel to the tissue, and the second electrode providing a path for the radio frequency energy to return from the tissue.

The invention further resides in the use of a tungsten disulphide material in an electrosurgical instrument to provide a surface which is resistant to the method comprising the adhering of tissue to the instrument. Typical electrosurgical instruments include forceps, scissors and scalpel blades.

The invention further resides in a method for manufacturing an electrosurgical instrument for the cutting and/or coagulating of tissue, the method comprising the steps of manufacturing at least one electrode from a metallic substrate, and disposing a coating of tungsten disulphide on to the at least one electrode.

The invention will now be described, by way of example only, with reference to the accompanying drawings, in which.

Figure 1:
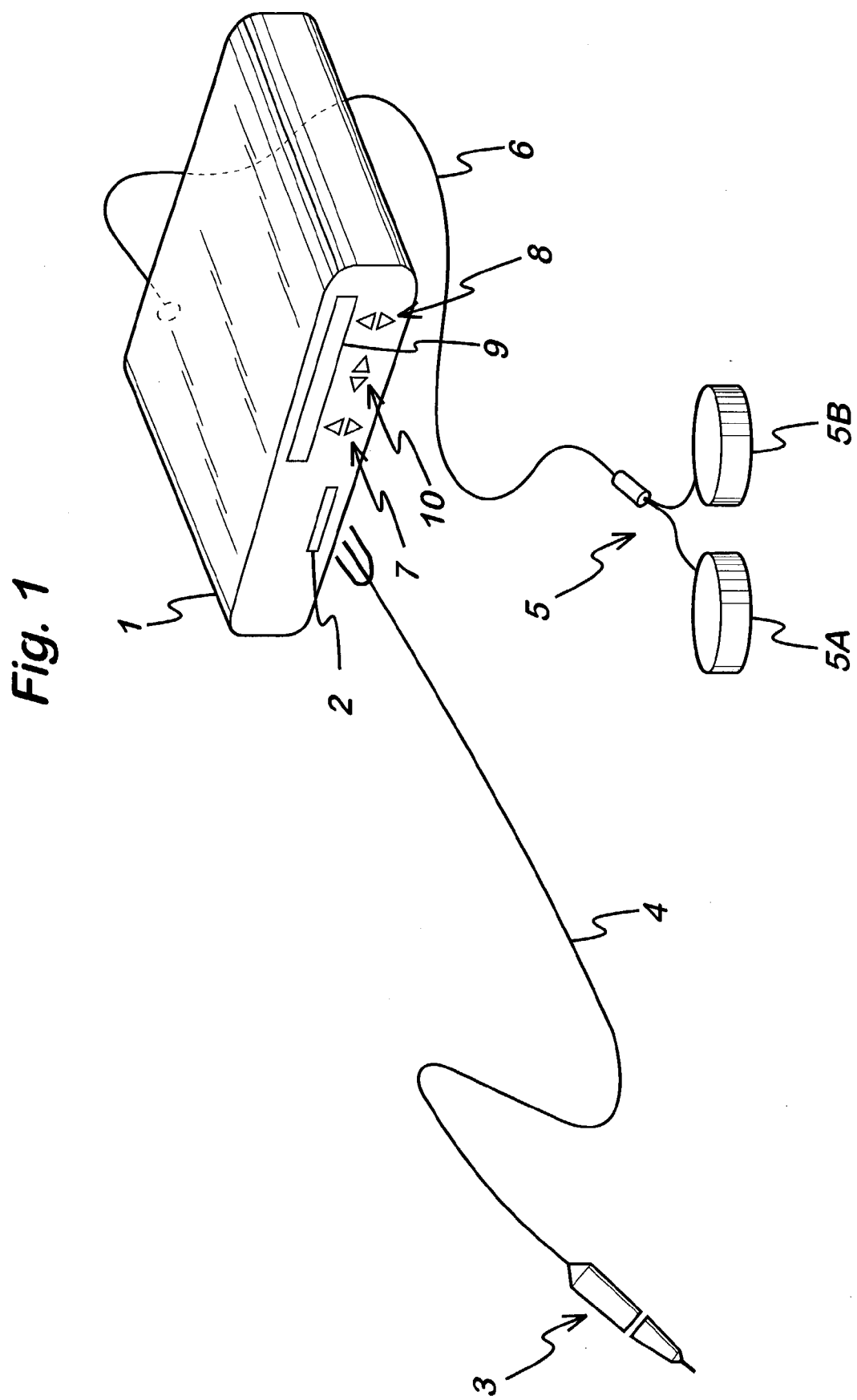
FIG. 1 is a schematic diagram of an electrosurgical system including an electrosurgical instrument constructed in accordance with the present invention.

Referring to FIG. 1, a generator 1 has an output socket 2 providing a radio frequency (RF) output for an electrosurgical instrument 3 via a connection cord 4. Activation of the generator 1 may be performed from the instrument 3 via the connection cord 4, or by means of a footswitch unit 5, as shown, connected to the rear of the generator by a footswitch connection cord 6. In the illustrated embodiment, the footswitch unit 5 has two footswitches 5A and 5B for selecting a coagulation mode and a cutting mode of the generator 1 respectively. The generator front panel has push buttons 7 and 8 for respectively setting coagulation and cutting power levels, which are indicated in a display 9. Push buttons 10 are provided as an alternative means for selection between coagulation and cutting modes.

Figure 2:
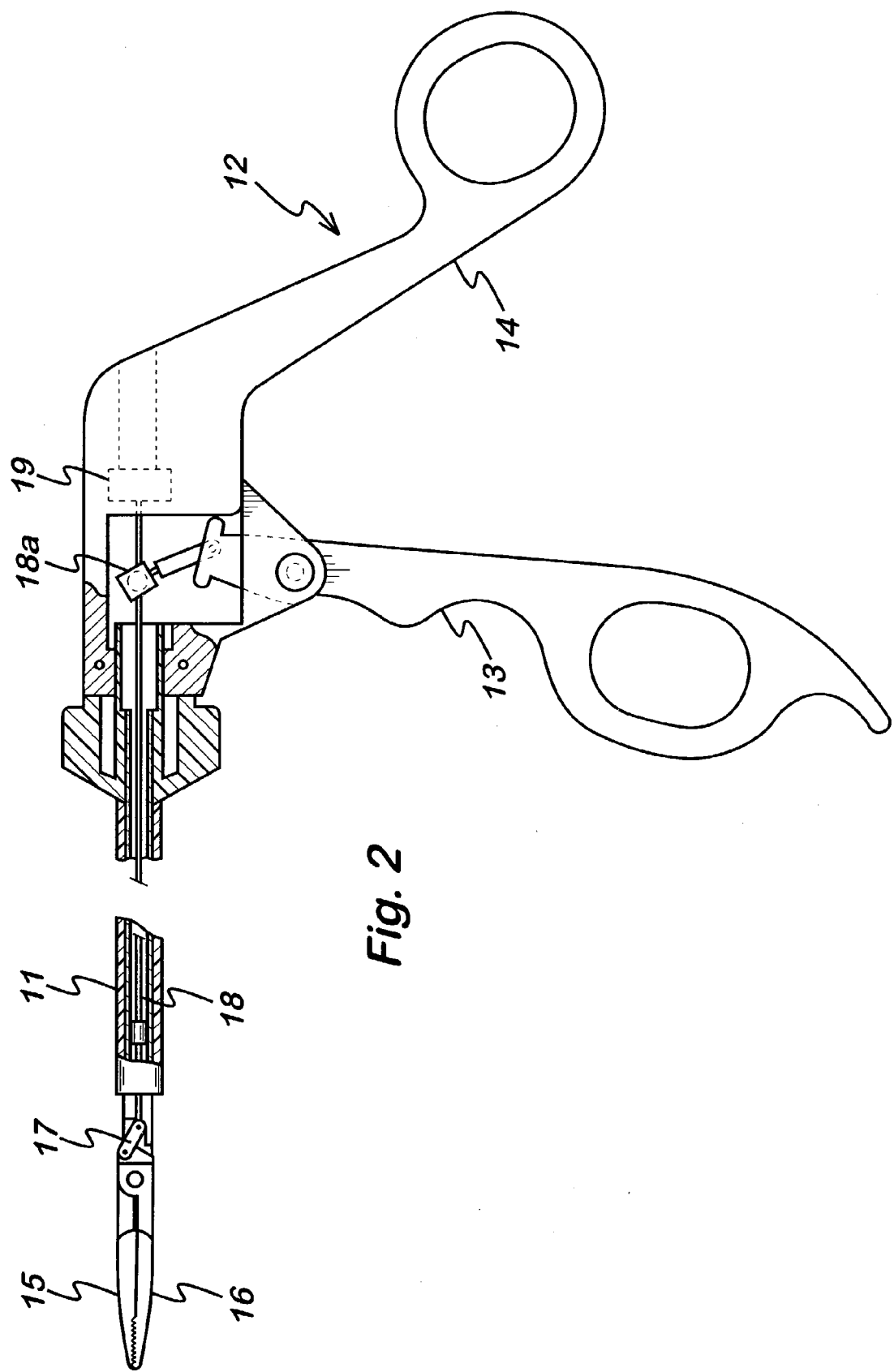
FIG. 2 is a schematic cross-sectional view of an electrosurgical forceps constructed in accordance with the present invention.

FIG. 2 shows a bipolar coagulating forceps device, which is one device which constitutes the instrument 3 in FIG. 1. The forceps comprises a tubular barrel 11 attached at its proximal end to a handle assembly 12, the handle assembly including first and second scissor handles 13 and 14, the handle 13 being pivotable with respect to the handle 14. At the distal end of the tubular barrel 11 is a pair of jaws 15 and 16, the jaws being pivotally movable one with respect to the other by means of a distal link assembly 17, operated by means a cable 18 running through the tubular barrel and attached to the handle 13 by means of a proximal link assembly 18a. In this way, the pivotal movement of the handle 13 with respect to the handle 14 causes the jaws 15 and 16 to open and close with respect to one another. This type of forceps device is entirely conventional, and a more detailed description of such a device is contained in U.S. Pat. No. 5,342,381 by way of example.

The jaws 15 and 16 are formed of steel, and are coated with a 0.5 micron coating of tungsten disulphide. The coating is applied by a spray coating process as carried out by Dicronite Dry Lube of Minnesota. In use, tissue to be coagulated is held firmly between the jaws 15 and 16, and a coagulating RF voltage is supplied to the jaws from the generator 1, via a connector 19 at the rear of the instrument. The RF signal passes through the tissue held between the jaws 15 and 16, heating it and causing the tissue to become coagulated.

The tungsten disulphide coating acts as a non-stick coating, significantly reducing the amount of tissue adhering to the jaws 15 and 16, even when the RF signal is applied to the tissue for an extended period of time. The tungsten disulphide coating was used in comparative tests against conventional non-stick coatings such as titanium nitride; and, while the tungsten disulphide did not have the glossy surface finish of titanium nitride, it matched (and in some cases even surpassed) it in terms of its ability to resist the adherence of tissue.

Figure 3:
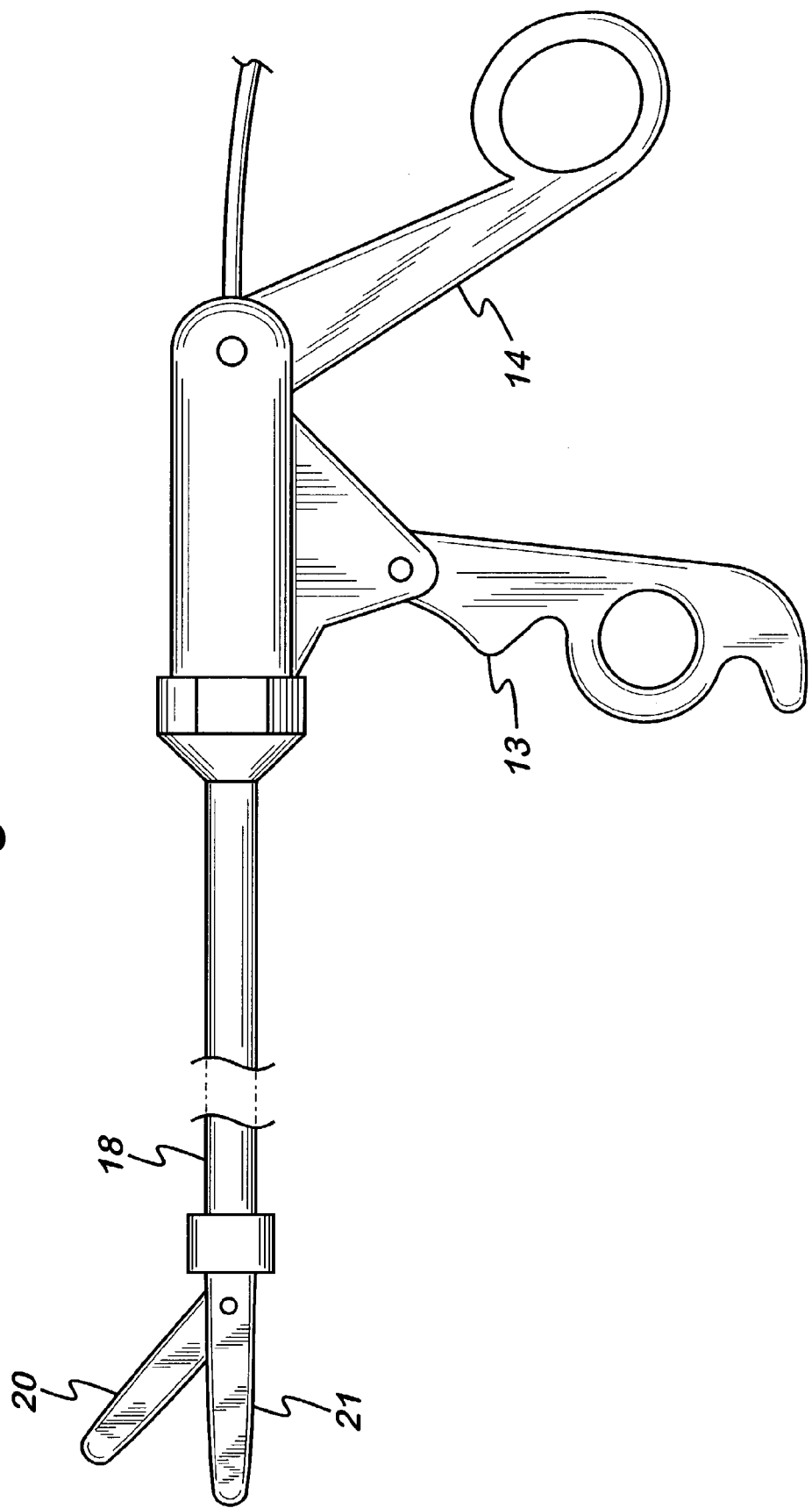
FIG. 3 is a schematic diagram showing a pair of bipolar scissors constructed in accordance with the invention.

FIG. 3 shows an alternative device in which the jaws are in the form of cutting blades 20 and 21. In this bipolar scissors device, which is again entirely conventional apart from the tungsten disulphide coating applied to the blades 20 and 21, the coating again provides improved resistance to the adherence of tissue to the blades. Such bipolar scissors devices can be used to both cut and coagulate tissue, and it is a common problem for their effectiveness to become impaired by the build-up of tissue on the blades thereof. The tungsten disulphide coating reduces this problem, and extends the useful operating life of the scissors device.

Figure 4:
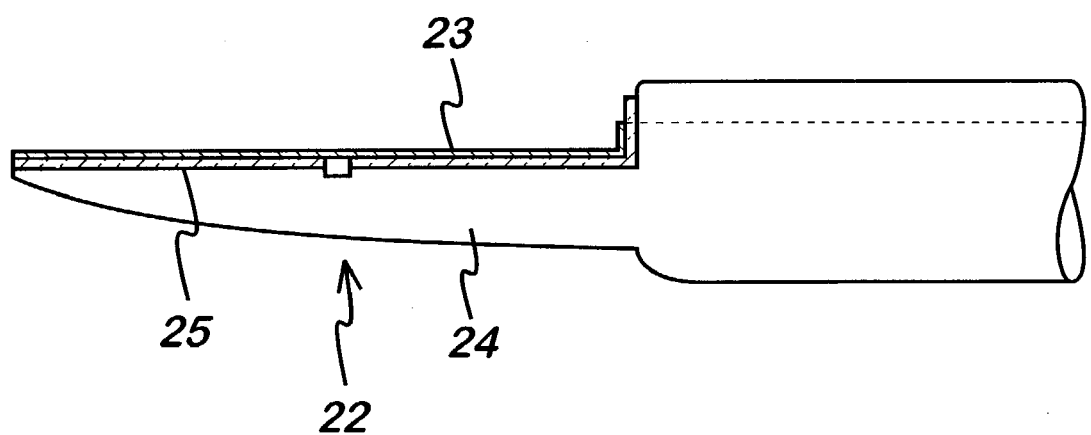
FIG. 4 is a schematic diagram of an embodiment of an electrosurgical cutting blade constructed in accordance with the invention.

FIG. 4 shows a further device which is in the form of a bipolar scalpel blade 22. The blade 22 has a first steel electrode 23 attached to a second steel electrode 24 via an insulating spacer 25. In use, the first electrode 23 obtains temperatures in excess of 100° C. in order that tissue adjacent to that electrode may be vaporised. Vaporised tissue tends to re-condense on the electrode 23, and tissue cut by that electrode can also become attached thereto. The provision of a tungsten disulphide coating on one or both of the electrodes 23 and 24 helps to avoid this build-up of tissue, once again prolonging the useful working life of the instrument.

What is claimed is:

1. An electrosurgical instrument including one or more electrode surfaces, at least one of the electrode surfaces being at least partially coated with tungsten disulphide.

2. An electrosurgical instrument for use in cutting and/or coagulating tissue, the instrument comprising at least one electrode, said at least one electrode comprising a substrate adapted to be connected to a source of radio frequency energy, and a tungsten disulphide coating disposed on the substrate.

3. An electrosurgical instrument according to claim 2, wherein the tungsten disulphide coating is a spray deposited coating.

4. An electrosurgical instrument according to claim 2, wherein the instrument is a bipolar electrosurgical instrument comprising first and second electrodes, the first electrode providing a path for the radio frequency energy to travel to the tissue, and the second electrode providing a path for the radio frequency energy to return from the tissue.

5. An electrosurgical instrument according to claim 4, wherein the instrument is a forceps instrument.

6. An electrosurgical instrument according to claim 4, wherein the instrument is a scissors instrument.

7. An electrosurgical instrument according to claim 4, wherein the instrument is a scalpel instrument.

8. A method for manufacturing an electrosurgical instrument for the cutting and/or coagulating of tissue, the method comprising the steps of manufacturing at least one electrode from a metallic substrate, and disposing a coating of tungsten disulphide on to said at least one electrode.

* * * * *